United States Patent [19]
Bruening et al.

[11] Patent Number: 6,054,711
[45] Date of Patent: Apr. 25, 2000

[54] METHODS FOR IDENTIFYING BIOLOGICAL MACROMOLECULE INTERACTIONS WITH COMPOUNDS, PARTICULARLY IN COMPLEX MIXTURES

[75] Inventors: Reimar C. Bruening, Cambridge, Mass.; Shannon Marshall, Pasadena, Calif.

[73] Assignee: Millennium Pharmaceuticals, Inc., Cambridge, Mass.

[21] Appl. No.: 08/969,186

[22] Filed: Nov. 12, 1997

[51] Int. Cl.[7] .................................................. G01N 21/35
[52] U.S. Cl. ............................... 250/339.08; 250/339.12
[58] Field of Search ....................... 250/339.08, 339.12; 436/171

[56] References Cited

U.S. PATENT DOCUMENTS

| | | | |
|---|---|---|---|
| 5,519,220 | 5/1996 | Truett | 250/339.08 |
| 5,539,207 | 7/1996 | Wong | 250/339.08 |
| 5,578,499 | 11/1996 | Ismail | 250/339.08 |

OTHER PUBLICATIONS

Tomasz et al., "Isolation and Structure of a Covalent Cross–Link Adduct Between Mitomycin C and DNA", Science 235: 1204–1208, Mar. 1987.

Barth et al., "Infrared Spectroscopic Signals Arising from Ligand Binding and Conformational Changes in the Catalytic Cycle of Sarcoplasmic Reticulum Calcium ATPase", Biochem. Biophys. Acta 1057:115–123, Mar. 1991.

*Primary Examiner*—Constantine Hannaher
*Attorney, Agent, or Firm*—Fish & Richardson, P.C.

[57] ABSTRACT

Methods for determining whether a biological macromolecule binds to a compound are disclosed. The methods include: a) obtaining a Fourier-Transform Infrared spectrum of a solution which contains a biological macromolecule and obtaining a Fourier-Transform Infrared spectrum of a solution which includes a compound; b) obtaining a Fourier-Transform Infrared spectrum of a solution which contains the biological macromolecule and compound of step a); c) subtracting the Fourier-Transform Infrared spectrum of the biological macromolecule of step a) and the Fourier-Transform Infrared spectrum of the compound of step a) from the Fourier-Transform spectrum of step b) to determine a subtracted index; and d) determining that the compound of step a) binds to the biological macromolecule of step a) when the subtracted index of step c) is not equal to zero.

20 Claims, 11 Drawing Sheets

METHODS FOR IDENTIFYING BIOLOGICAL MACROMOLECULE INTERACTIONS WITH COMPOUNDS, PARTICULARLY IN COMPLEX MIXTURES

The present invention is in the field of drug discovery. The present invention specifically provides methods for determining whether a compound interacts with a biological macromolecule in solution using Fourier-Transform Infrared Spectroscopy (FT-IR), particularly microscopic FT-IR.

BACKGROUND OF THE INVENTION

Fourier-Transform Infrared Spectroscopy (FT-IR) has been used to study conformational changes that occur in solid phase and film phase molecular structures (see e.g., Tomasz et al., Science 235:1204–1208 (1987) and Barth et al., Biochem. Biophys. Acta 1057:115–123 (1991)). However, it has not been apply to drug discovery, particularly in solution phase, with high through-put methods and small amounts of target (fmolar). Problems with high background and peak identification has been some of the reason that FT-IR spectroscopy has had limited fields of use. The present invention provides methods of using FT-IR spectroscopy, particularly differential, microscopic FT-IR spectroscopy, for drug discovery.

SUMMARY OF THE INVENTION

The present invention provides methods for determining whether a biological macromolecule binds to a compound. The methods of the present invention comprise the steps of:

a) obtaining an FT-IR spectrum of a solution comprising a biological macromolecule and a solution comprising a compound individually;

b) obtaining an FT-IR spectrum of a solution comprising a mixture of the biological macromolecule and the compound;

c) subtracting the FT-IR spectrum of the individual biological macromolecule and compound from the FT-IR spectrum of the mixture; and d) identifying a compound that binds to said biological macromolecule when the subtracted index of step c) is not equal to about 0.

In the preferred embodiments, the biological macromolecule contains amide bonds, such as a peptide or protein, the compound tested is present in a complex mixture of chemical entities, such as in a fungal fermentation broth, the FT-IR spectrum obtained and used in the analysis is from about 1700 $cm^{-1}$ to about 1500 $cm^{-1}$, microscopic FT-IR instrumentation is used, the biological macromolecule and compound are present in fmolar amounts, the spectrum from about 2000 to about 1700 $cm^{-1}$ and from about 1500 to about 1200 $cm^{-1}$ are used as a baseline noise reference, and data from each sample are collected in one second or less.

DESCRIPTION OF THE PREFERRED EMBODIMENTS

I. General Description

The present invention is based on the novel observation that differential Fourier-Transform Infrared Spectroscopy (FT-IR) can be used to identify whether a compound binds to a macromolecule in solution when it is previously unknown whether the two molecules interact. Particularly, the present invention demonstrates that the interaction of biological macromolecules with compounds can be determined using differential FT-IR, preferably microscopic FT-IR, and in particular when the biological macromolecule is a semi-pure or partially characterized protein, the compound tested is present in a complex mixture of compounds, the biological macromolecules are present in fmolar amounts and high through-put fluid handling equipment and methods are used.

II. Specific Embodiments

A. Methods For Detecting The Interaction Of A Biological Macromolecule With A Compound The present invention provides methods for determining whether a biological macromolecule binds to a compound, in solution, when it is unknown whether such binding occurs. In detail the method involves obtaining an FT-IR spectrum of a solution containing the biological macromolecule and the compound individually. In addition, an FT-IR spectrum of a solution containing a mixture of the biological macromolecule and the compound is obtained. The FT-IR spectrum of the mixture is then subtracted from the FT-IR spectrum of the individual biological macromolecule and compound. After subtraction, the resultant spectrum is analyzed to see if there is a shift in a peak, namely, when the subtracted index of mixture from the individual components is not equal to about 0. A peak shift indicates that the compound bound to the biological macromolecule.

As used herein, a biological macromolecule refers to any chemical entity produced in a biological system that has an identifiable FT-IR spectrum which shifts upon the binding of another chemical entity. The preferred biological macromolecules for use in the present method contain amide bonds, particularly ones contained in amino acids, peptides and proteins. However, other biological macromolecules that can be used in the present method include, but are not limited to, nucleic acid molecules such as DNA and RNA, lipids, and carbohydrates. A skilled artisan can readily determine whether a particular biological macromolecule can be used in the present method.

The biological macromolecule used in the present method can be an isolated biological macromolecule, such as a biological macromolecule that has been purified to homogeneity, a partially isolated biological macromolecule, such as a biological macromolecule which is present in a mixture after single purification step, or present in a complex mixture, such as that found in a cellular or tissue extract. Examples of complex mixtures containing a biological macromolecule include, but are not limited to, a cellular extract, a tissue extract, a fermentation broth of a microorganism, a fermentation broth of a cell culture or a fermentation broth of a tissue culture. The present invention is particularly useful with biological macromolecules such as protein, which are present in partially isolated form, such as single step purified recombinant protein.

Further, the biological macromolecule can be fully characterized, such as a protein whose activity is known and/or a protein with a known amino acid sequence. However, the present invention is particularly useful with partially characterized biological macromolecule, such as a biological macromolecule which can be identified as being present in a sample but whose biological activity is unknown or difficult to assay. In such a use, the present invention provides a powerful method of drug screening for biological macromolecules that are pharmaceutical targets whose activity is difficult to measure.

As used herein, a compound refers to any molecular entity. Particularly important molecular entities include, but are not limited to, small molecules, such as organic compounds, aromatic compounds and vitamin derivatives, as well as larger molecules, such as complex natural products and peptides. A skilled artisan can readily appreciate that any chemical entity that can be manipulated in solution can be used in the present method.

The compound can be an isolated compound, such as a compound that is present as a single chemical entity, a partially isolated compound, or present in a complex mixture of many different chemical entities. Complex mixtures include, but not limited to, a cellular extract, a tissue extract, a fermentation broth of a microorganism, a fermentation broth of a cell culture and a fermentation broth of a tissue culture. The present invention is particularly useful in screening complex mixtures of compounds consisting of more than 100 chemical entities, preferably more than 1,000 chemical entities, such as that present in a fungal fermentation broth or a plant or other natural product extract.

Further, the compound used in the present method can be a fully characterized compound, such as a compound with a known structure, biological activity and/or composition, or the compound can be an unknown test compound whose presence can be detected, but whose structure, biological activity and/or composition is unknown. In such a use, the present invention provides a powerful method of drug screening for novel bioactive compounds for potential pharmaceutical use.

The compounds and biological macromolecules used in the present methods are in solution phase. A skilled artisan can readily adapt known buffer systems for use with a wide variety of compounds and biological macromolecules.

The present method is used to determine whether a compound binds to a biological macromolecule. As used herein, a compound is said to bind a biological macromolecule when the compound becomes associated with, either covalently, non-covalantly, with them biological macromolecule and the interaction causes an identifiable in the FT-IR spectrum of the biological macromolecule. For example, in the Examples it is shown that a shift in the FT-IR spectrum occurs when a compound denoted as UK328715, an antifungal agent, binds to N-myristoyl transferase (NMT), an enzyme which is of interest as an antimicrobial and anticancer drug target.

As discussed above, the method of the present invention relies on the use FT-IR, and in particular, differential FT-IR. FT-IR is well known in the art and has been described in detail elsewhere (see, e.g., Barth et al., supra). A skilled artisan can readily adapt and use commercially available FT-IR apparatus and data collection and analysis instrumentation for use in the present method.

Figure 5:
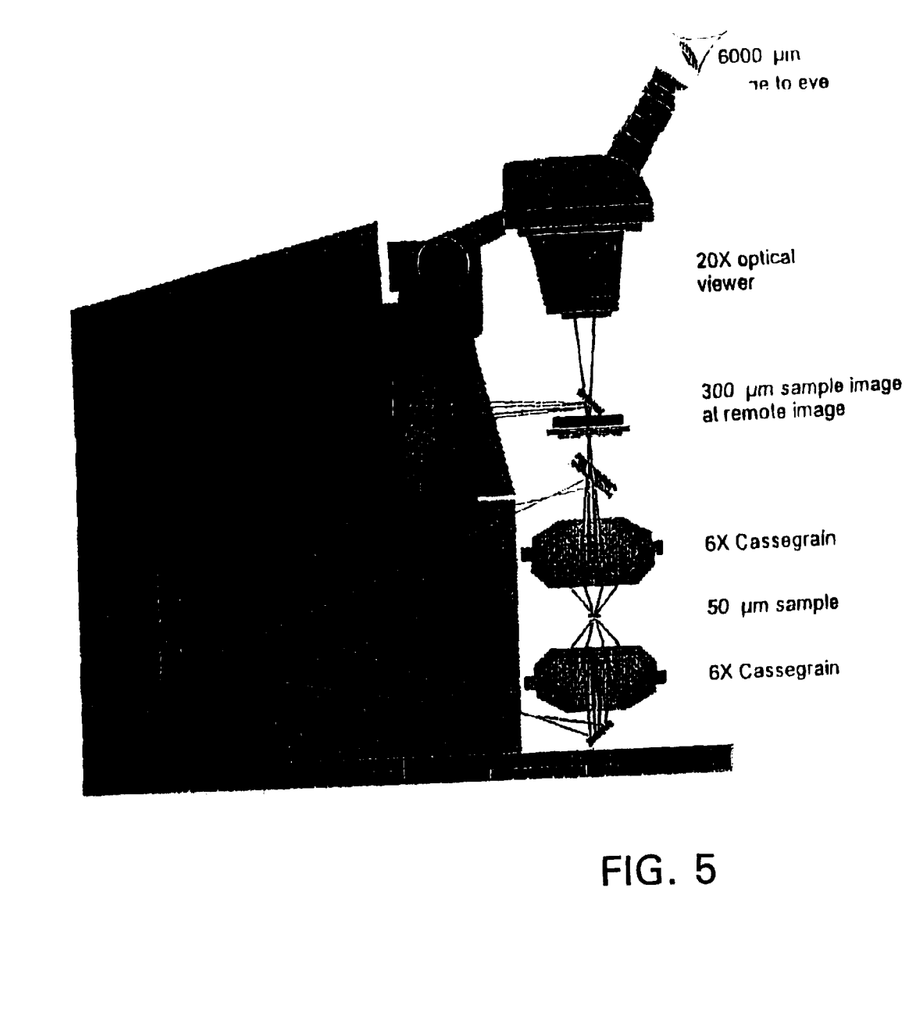
FIG. 5 shows a diagram of a microscopic FT-IR apparatus.
Figure 6:
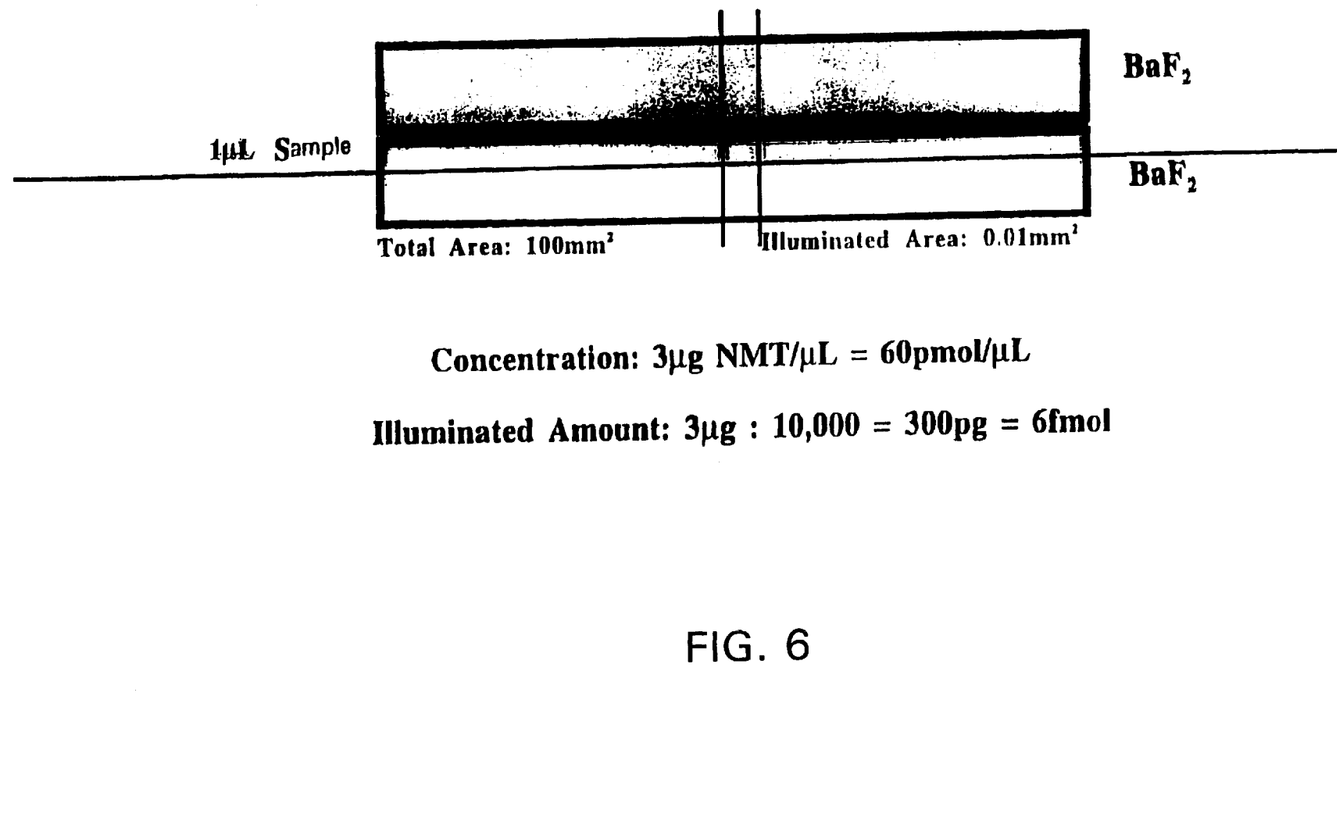
FIG. 6 shows the volume and analysis area of a typical microscopic FT-IR instrument.

In a particularly preferred embodiment, the FT-IR used is microscopic FT-IR. (FIG. 5). Microscopic FT-IR has been used primarily for surface analysis in material science, geology and crystallographic applications. However, microscopic FT-IR has not been used to determine whether a biological macromolecule binds to a compound, particularly in complex mixtures or in high-throughput screening methods. With microscopic FT-IR, biological macromolecules can be used in the range of from about 3 fmolar, to about 100 pmolar, namely from about 150 pg to about 5 $\mu$g of biological macromolecule which is all that is needed for each reaction mixture. One example of a microscopic FT-IR apparatus is the Perkins-Elmer I-series computerized IR-microscope with IMAGE software.

The FT-IR spectrum used in the present method will be based on the signature FT-IR spectrum of the biological macromolecule used. For the preferred biological macromolecules, those having amide bonds such as peptides and proteins, the FT-IR spectrum obtained for analysis will comprise the spectrum from about 1700 $cm^{-1}$ to about 1500 $cm^{-1}$. A skilled artisan will be able to select an appropriate FT-IR spectrum range to be analyzed based on the nature and complexity of the biological macromolecule without undue experimentation. For proteins, typical spectral peaks within the signature range will vary from about 0.05 to about 0.10 absorbance units above baseline.

The spectra of the biological macromolecule and compounds are determined separately and as a mixture of the biological macromolecule and compound. High throughput screening methods can be combined with FT-IR in the present method, particularly microscopic FT-IR, and allow for screening of multiple samples in short periods of time. In a preferred use, high-throughput screening methods and microscopic FT-IR analysis is used to collect data in less than about one second per sample. This allows the present invention to be used to screening multiple compounds, preferably more than 100, more preferably more than 1,000, compounds for the ability to bind a biological macromolecule in a relatively short period of time. A skilled artisan can readily adapt computer controlled robotic fluid handling methods, apparatus and software for assembling a high through-put screening system that is based on the methods of the present invention.

A part of the present method, the FT-IR spectrum of the compound and the biological macromolecule is obtained separately. Once obtained, the spectrum can be stored in a computer data base and used with FT-IR spectrum obtained from mixture generated and analyzed at a later date. In one such use, the FT-IR spectrum of each member of a chemical library, such as a library comprising more than 1,000 chemical entities, is determined and stored for use each time the library is screened against a different biological macromolecule.

In a preferred embodiment, the difference spectrum outside the signature spectrum of the biological macromolecule is used as a baseline for signal to noise ratio adjustment. In such a use, the noise produced by the subtraction of the biological macromolecule and the compound spectra from the spectrum of the biological macromolecule/compound mixture outside the signature range of the biological macromolecule (the signature range being the spectral range that contains the spectral peak that shifts upon biological macromolecule/compound binding) is used as a threshold level. Spectral peaks within the signature range (from about 1700 $cm^{-1}$ to about 1500 $cm^{-1}$ for peptide or protein biological macromolecules) which are less than the absorbance found in the spectral peaks outside the signature range, preferably less than two times the absorbance, most preferably less than three times the absorbance, are removed form the data which is analyzed (subtracted: discussed in detail below). For the preferred targets that have amide bonds, such as peptides and proteins, the spectrum from about 2000 to about 1700 $cm^{-1}$ and the spectrum from about 1500 $cm^{-1}$ to about 1200 $cm^{-1}$ are used as a baseline noise reference. Subtraction residues ("peaks") within this range are used as a threshold and "peaks" within the signature range (from about 1700 $cm^{-1}$ to about 1500 $cm^{-1}$) which are less than the "peak" height in the noise range, preferably less than two times the "peak" height in the noise range, most preferably less than three times the "peak" height in the noise range, are excluded from further analysis. Preferably, the signal to noise ratio adjustment described above is performed in a computer designed to collect and process the FT-IR data. A skilled artisan can readily use commercially available computer hardware and software with the herein described method, for example the Perkins-Elmer IMAGE software.

In the present use of differential FT-IR analysis, the spectrum of the individual biological macromolecule and compound is subtracted from the spectrum of the mixture, preferably after signal to noise ratio adjustment. Preferably, a computer controlled system is used to electronically subtract the spectrum. A variety of commercially available software packages can be adapted for use in the present methods.

After the subtracted spectrum is obtained, the subtracted spectrum is analyzed to see if the spectrum is not equal to zero, namely whether there is a significant subtraction residue, "peak", remaining in the signature spectral range which is greater than the noise "peaks" outside the signature range, preferably two times greater than the noise, most preferably three times greater than the noise. When the compound and the biological macromolecule do not interact, the spectrum of the individual reactants are the same as that of the mixture and the resultant subtracted spectrum is equal to 0, it will not have a significant subtraction residue ("peak") within the signature range above the background noise threshold.

However, if the biological macromolecule binds the compound, the interaction will result in a detectable difference in the individual spectrum compared to the mixture based upon changes in the three dimensional structure of the biological macromolecule after binding to the compound. Specifically, the individual biological macromolecule will have one or more spectral peaks within the signature range at a given absorbance and the bound biological macromolecule/compound will have one or more spectral peaks at a different absorbance within the signature range. Preferably, the difference in peak absorbance in the biological macromolecule compared to the bound biological macromolecule/compound complex will be at least 1 $cm^{-1}$, preferably, at least 2.5 $cm^{-1}$, most preferably at least 5 $cm^{-1}$.

The method of the present invention is particularly useful in drug discovery, particularly in identifying agents that bind to and modulate the activity of a biologically important target. In such a use, a biological macromolecule which is a candidate as a drug target is screened against single compounds, complex mixtures of compounds, such as that present in a fungal fermentation broth, or a library of compounds to identify a compound that binds to the target. Such a method can be used as a first step in the identification of a pharmaceutically active agent.

Biological macromolecules that are particularly useful in the present context of drug discovery include, but are not limited to enzymes and soluble proteins, receptors, nucleic acid molecules, etc.

The present method is also useful in the identification of a unknown ligand of an isolated or identified receptor. In such a use, a receptor is mixed with a complex mixture and the presence or absence of a binding ligand is determined. In a preferred use, the complex mixture will be an extract of a biological cell, tissue or organism that is suspected of possessing the ligand. Once the presence of a ligand or potential ligand is detected, the method of the present invention can then be used as an assay during the purification of the ligand, e.g., by analyzing samples obtained during a purification process for the presence of the binding ligand.

In a mirror use, the method of the present invention can be used to identify an unknown receptor for a known ligand.

The present method is also useful in identifying selective compounds, namely compounds that bind to one biological macromolecule and not to another biological macromolecule in the mixture. For example, it is at times important to find compounds that bind to and alter one biological macromolecule while not binding to a related biological macromolecule. For example, a agent can be identified that binds to a viral or microorganism protein while not binding to the human homologue.

The following examples are intended to illustrate, but not to limit, aspects of the present invention.

EXAMPLES

Materials and Methods

Figure 1:
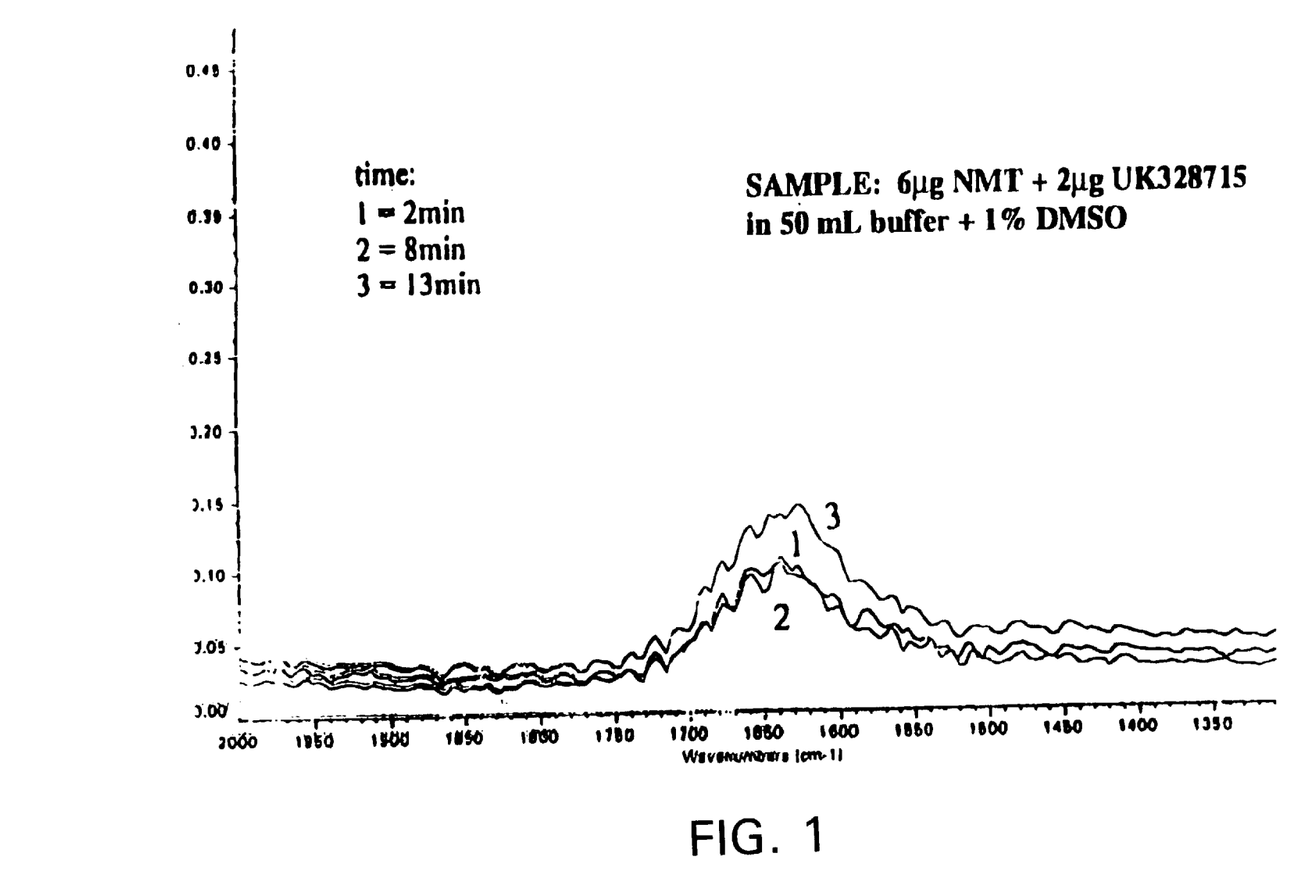
FIG. 1 shows the differential FT-IR spectrum of a biological macromolecule (NMT) with a binding compound (UK328715) under various timed attenuated total reflection conditions.

For all experiments, a circular ATR flow cell with a 50 ul volume was used (Spectratech, Inc.). FIG. 1 shows the differential FT-IR spectrum of NMT (6 μg) mixed with UK328715 (2 μg) in 50 ul buffer with 1% DMSO under various timed attenuated total reflection conditions (peak 1=2 min, peak 2=8min, and peak 3=13min:differential FT-IR is the FT-IR spectrum of the mixture minus the FT-IR spectra of the individual components).

Figure 2:
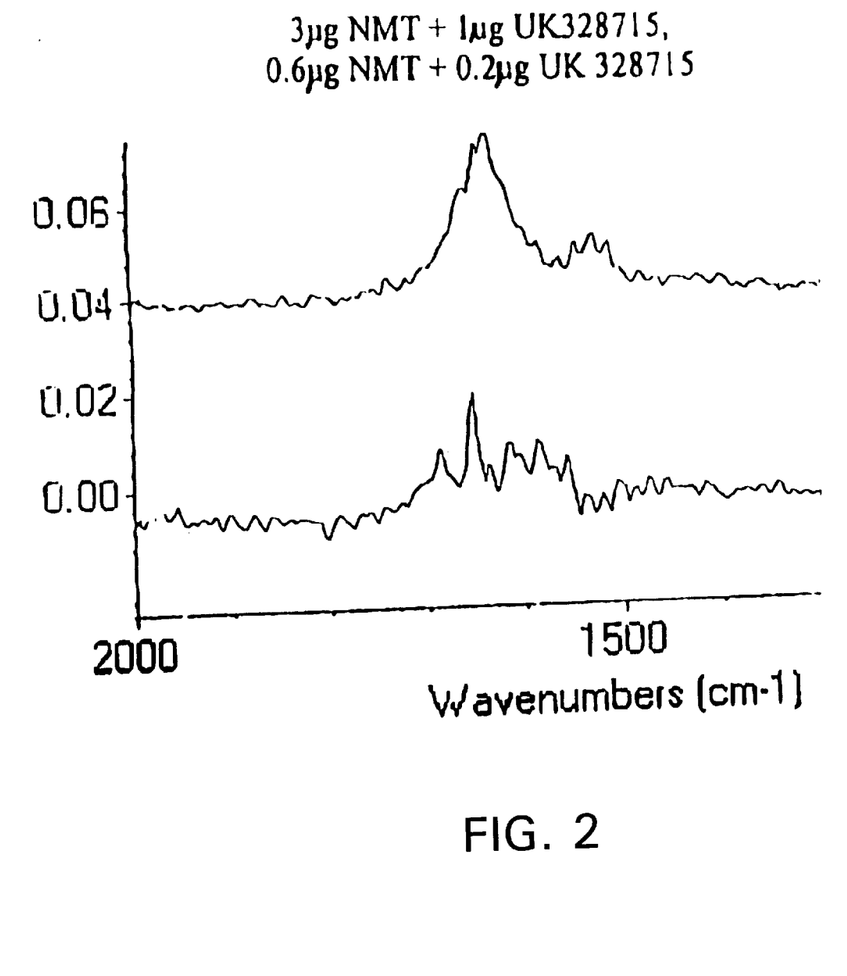
FIG. 2 shows the differential FT-IR spectrum for different biological macromolecule/compound concentrations.

Two different concentration of NMT/UK328715 were used to determine the sensitivity of differential FT-IR to detect peak shifts. FIG. 2 shows the differential FT-IR spectra for 3 μg NMT and 1 μg UK328715, in 50 ml buffer, (upper trace) and for 0.6 μg NMT and 0.2 μg UK328715, in 50 μl buffer (lower trace).

Figure 3:
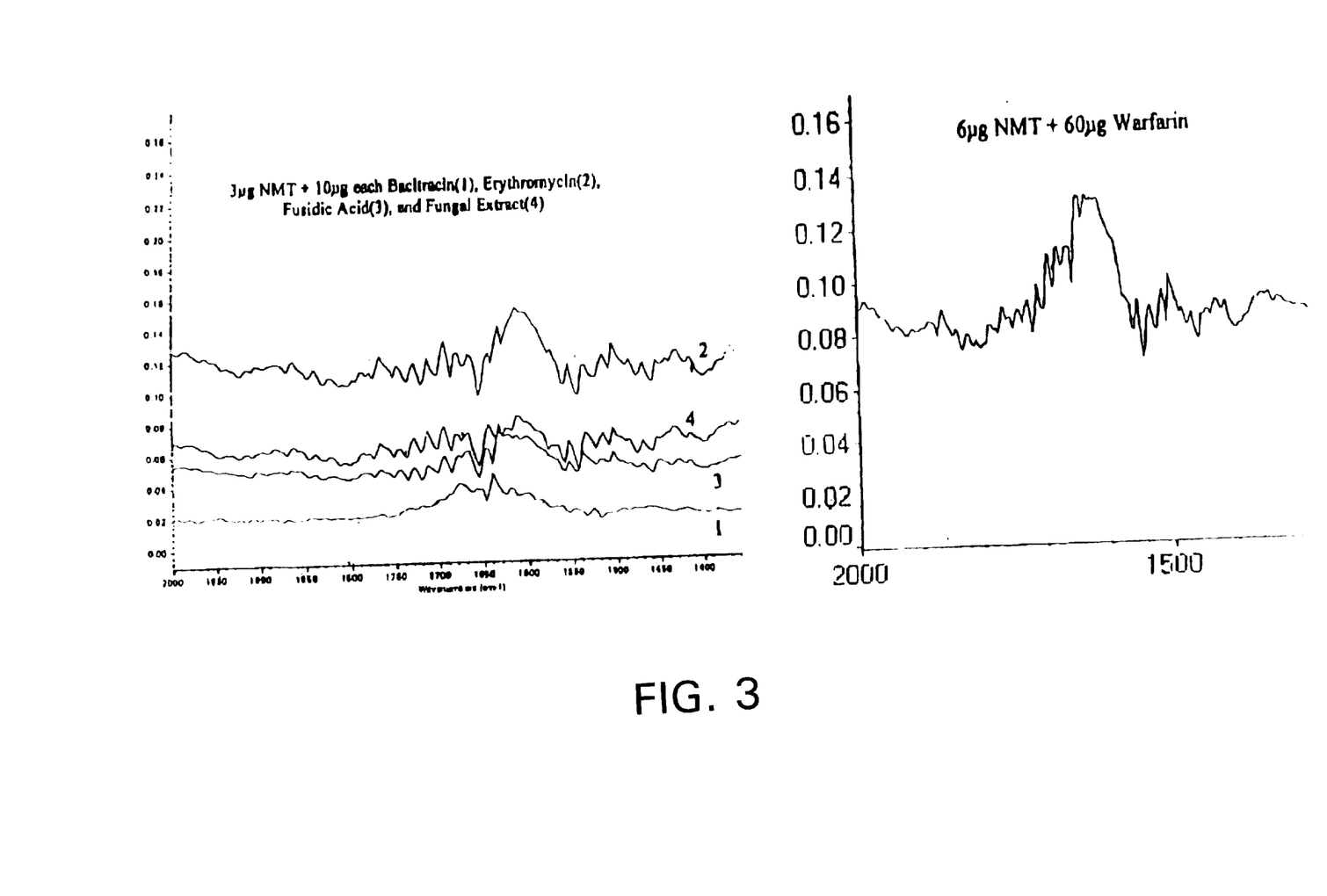
FIG. 3 shows the differential FT-IR spectra for a biological macromolecule mixed with non-binding compounds and non-specific binding compounds.
Figure 4:
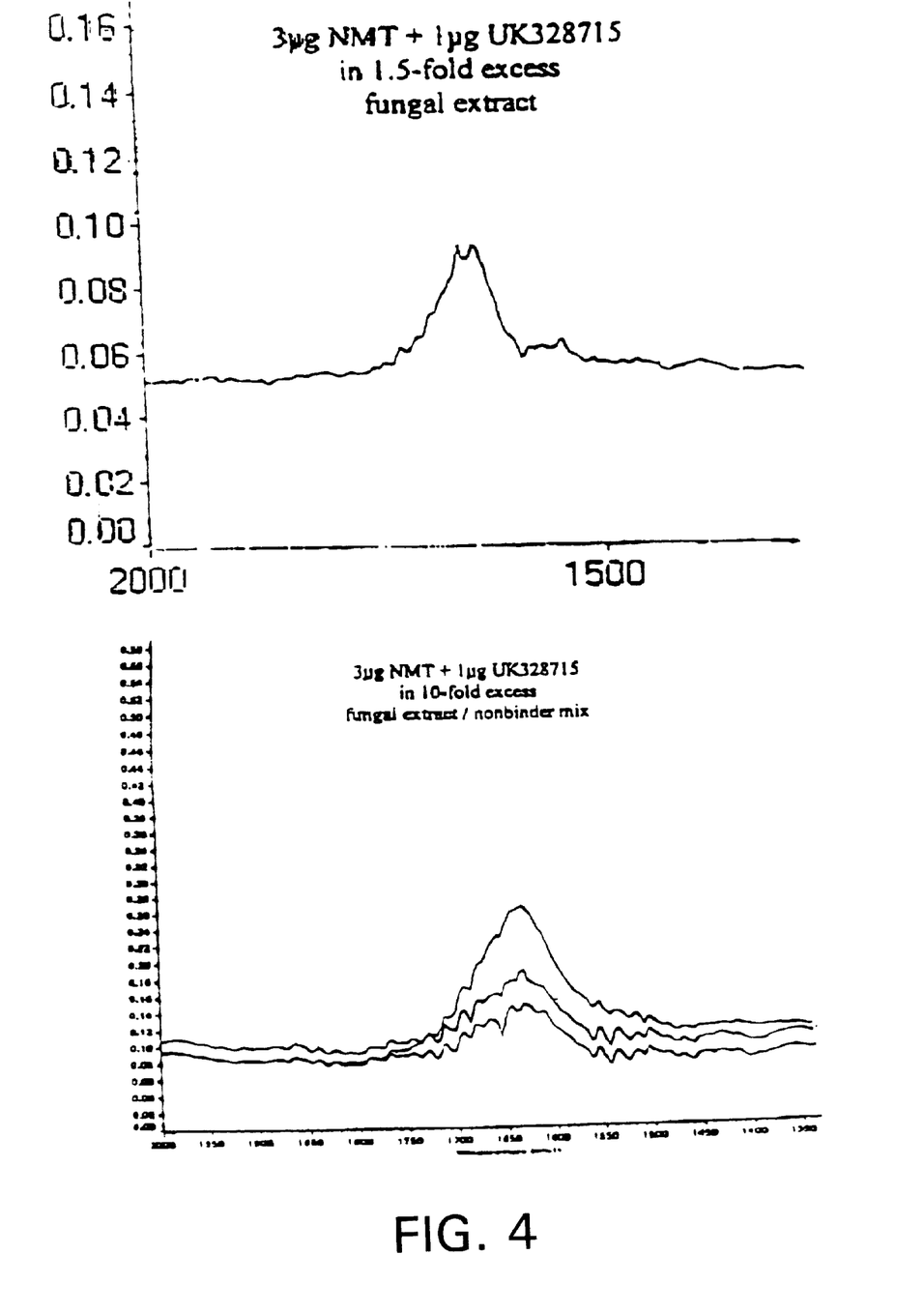
FIG. 4 shows the differential FT-IR spectra detecting the binding of a compound in a complex mixture (fungal extract spiked with UK328715) to a biological macromolecule (NMT).

To show that non-binding compounds do not significantly influence the FT-IR spectrum of a biological macromolecule when mixed with the biological macromolecule, 3 μg of NMT was mixed with 10 μg each of Bacitracin (trace 1), Erythromycin (2), Fusidic Acid (3) and a fungal extract (4) and a differential FT-IR spectrum of each sample was obtained (FIG. 3). The non-binding compounds did not alter the spectrum of NMT. However, a nonspecific binding compound, Warfarin (60 μg), did produce a detectable peak shift for NMT.

To show the ability of differential FT-IR to detect protein/compound binding in a complex sample, 1 μg UK328715 was added to a fungal extract (non-binding), mixed with NMT and a differential FT-IR spectrum was generated. The spiked fungal extract produced a peak shift for NMT.

Figure 7:
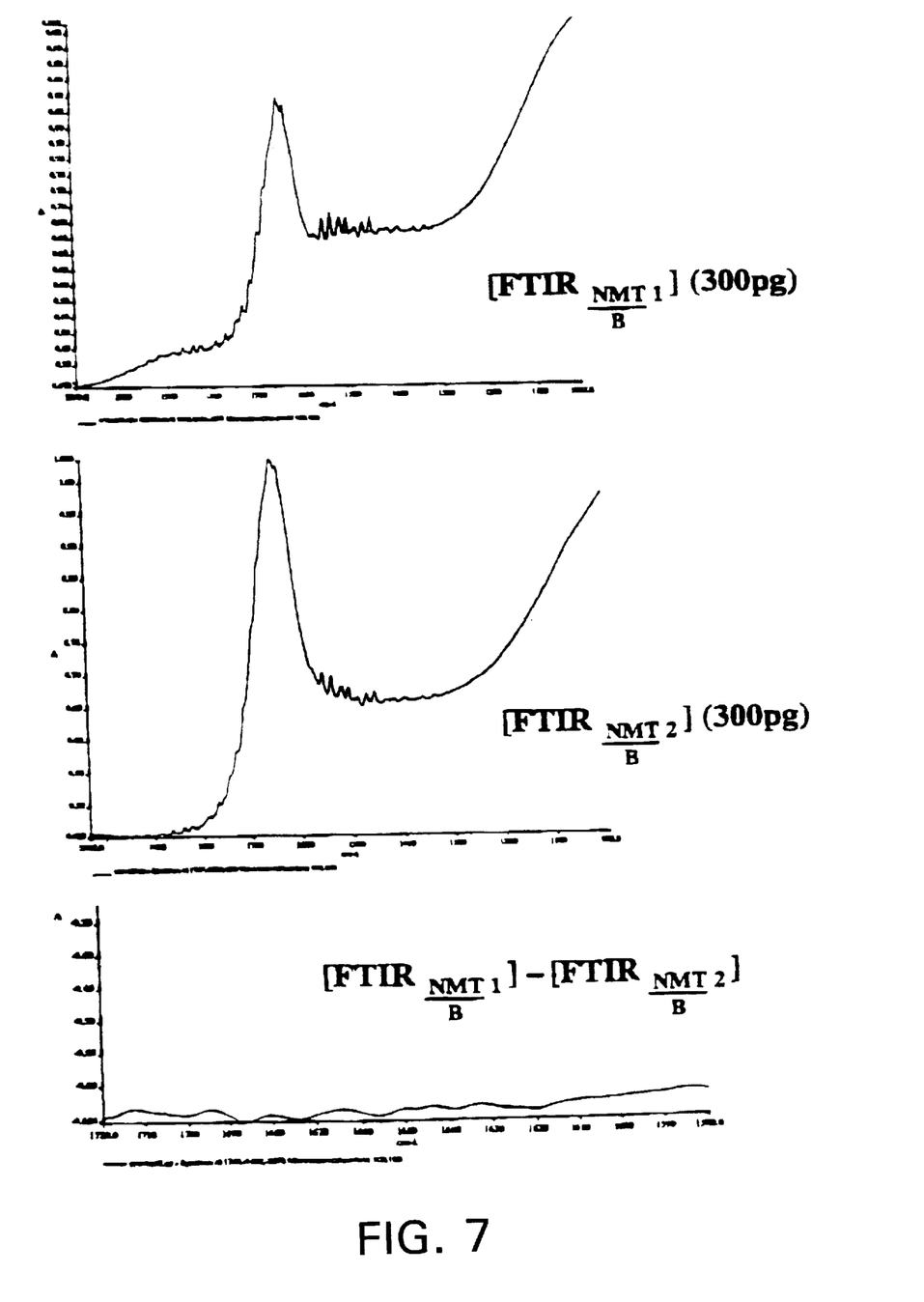
FIG. 7 shows a determination of background noise in a microscopic FT-IR subtractive spectrum obtained two separately prepared samples of NMT.

To determine the background noise in a Perkin-Elmer microscopic FT-IR apparatus, two separate spectra were obtained for a solution containing 300 pg of NMT (upper two spectra of FIG. 7). The two spectra were subtracted from each other, yielding a nearly flat background.

Figure 8:
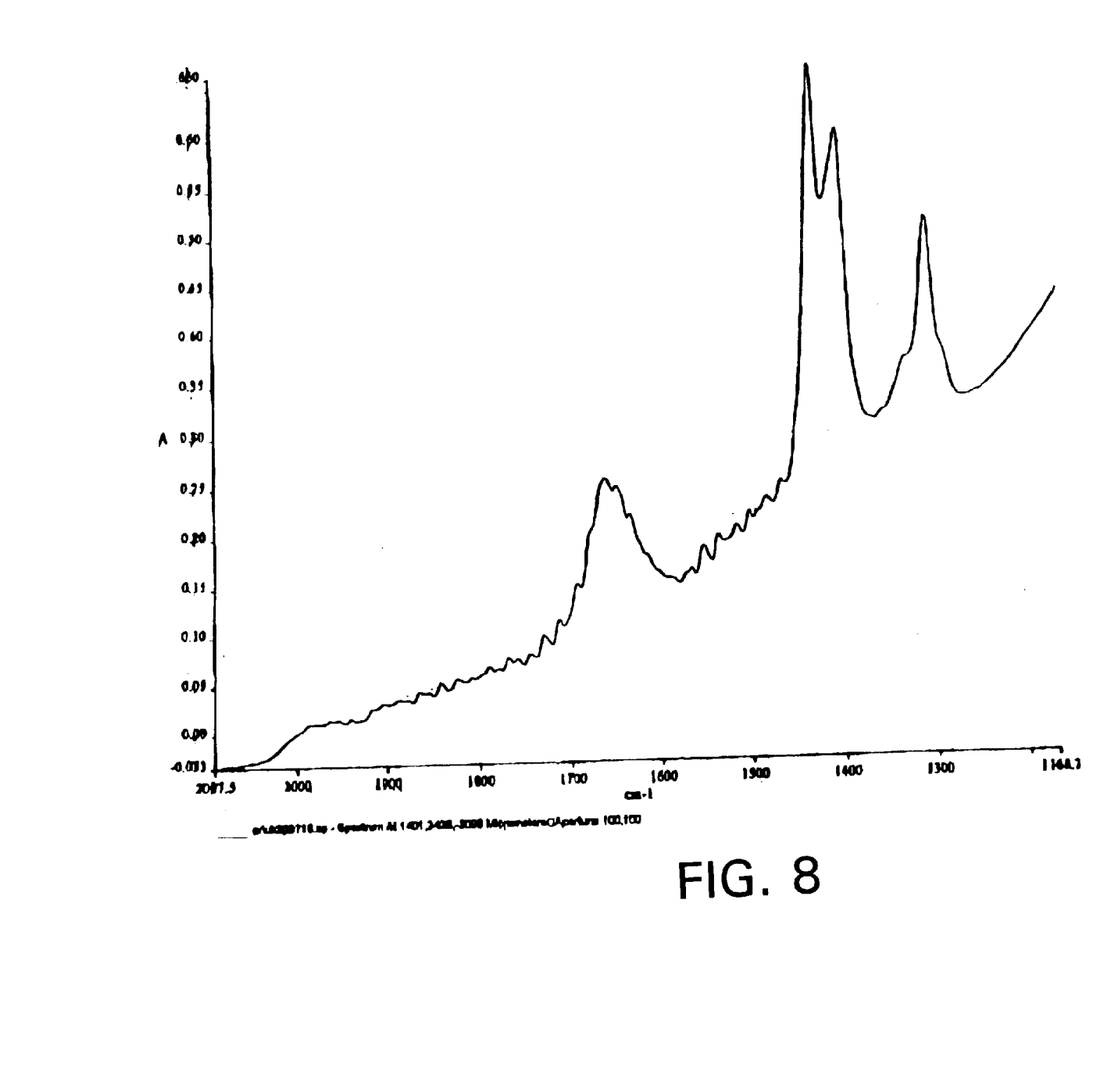
FIG. 8 shows microscopic FT-IR spectrum of UK328715.
Figure 9:
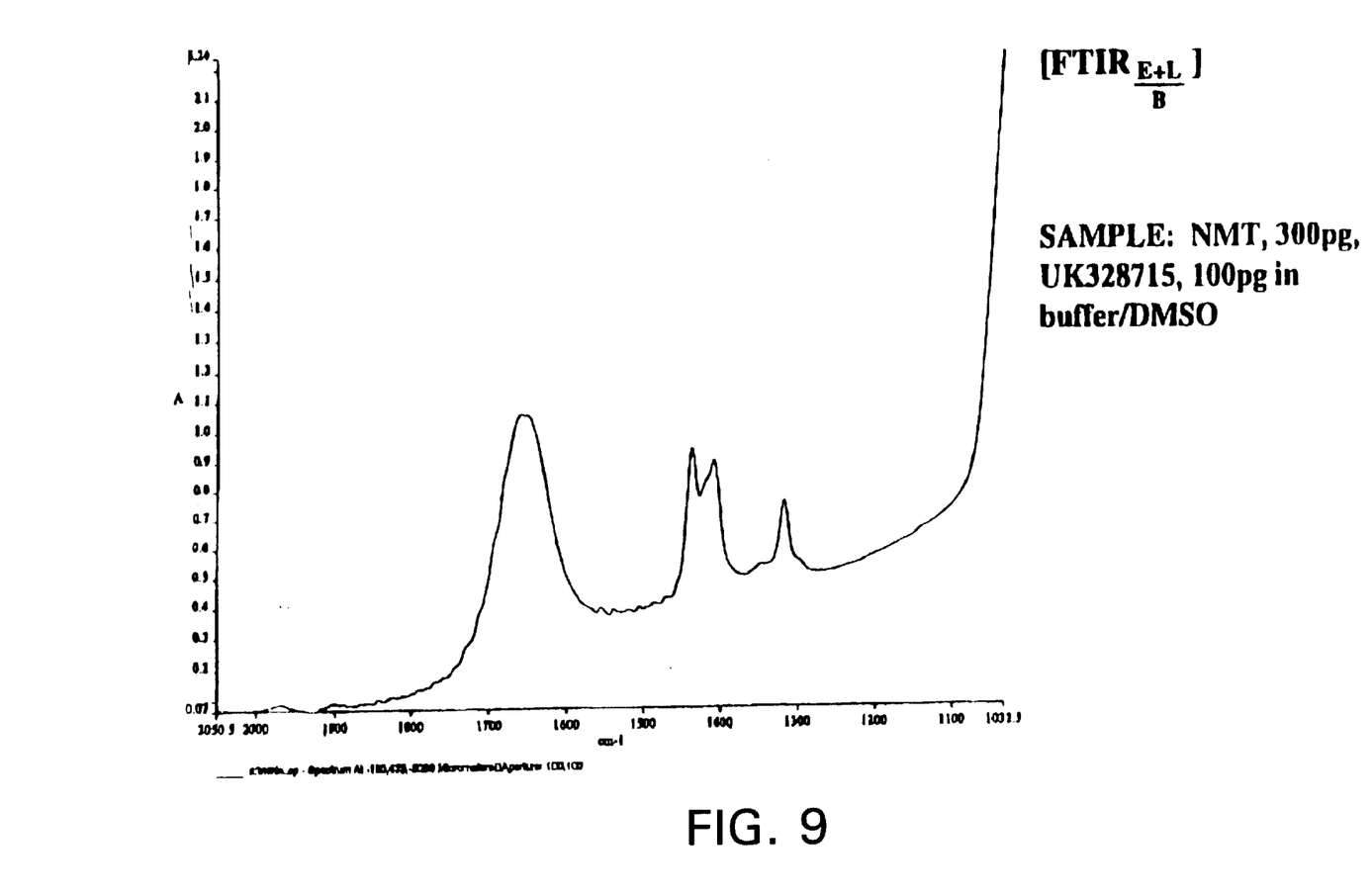
FIG. 9 shows microscopic FT-IR spectrum of a mixture of NMT and UK328715.
Figure 10:
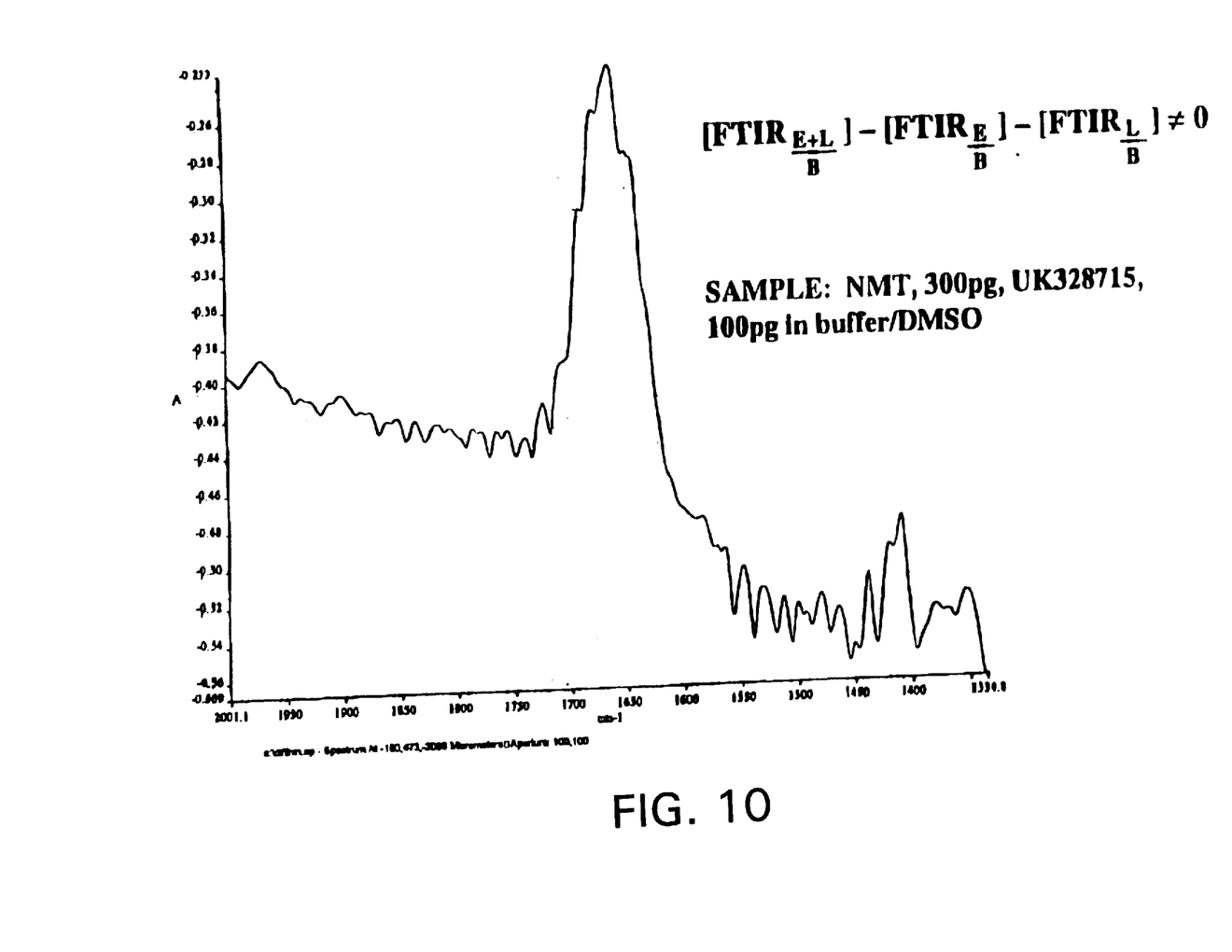
FIG. 10 shows the differential microscopic FT-IR spectrum of a mixture of NMT and UK328715.
Figure 11:
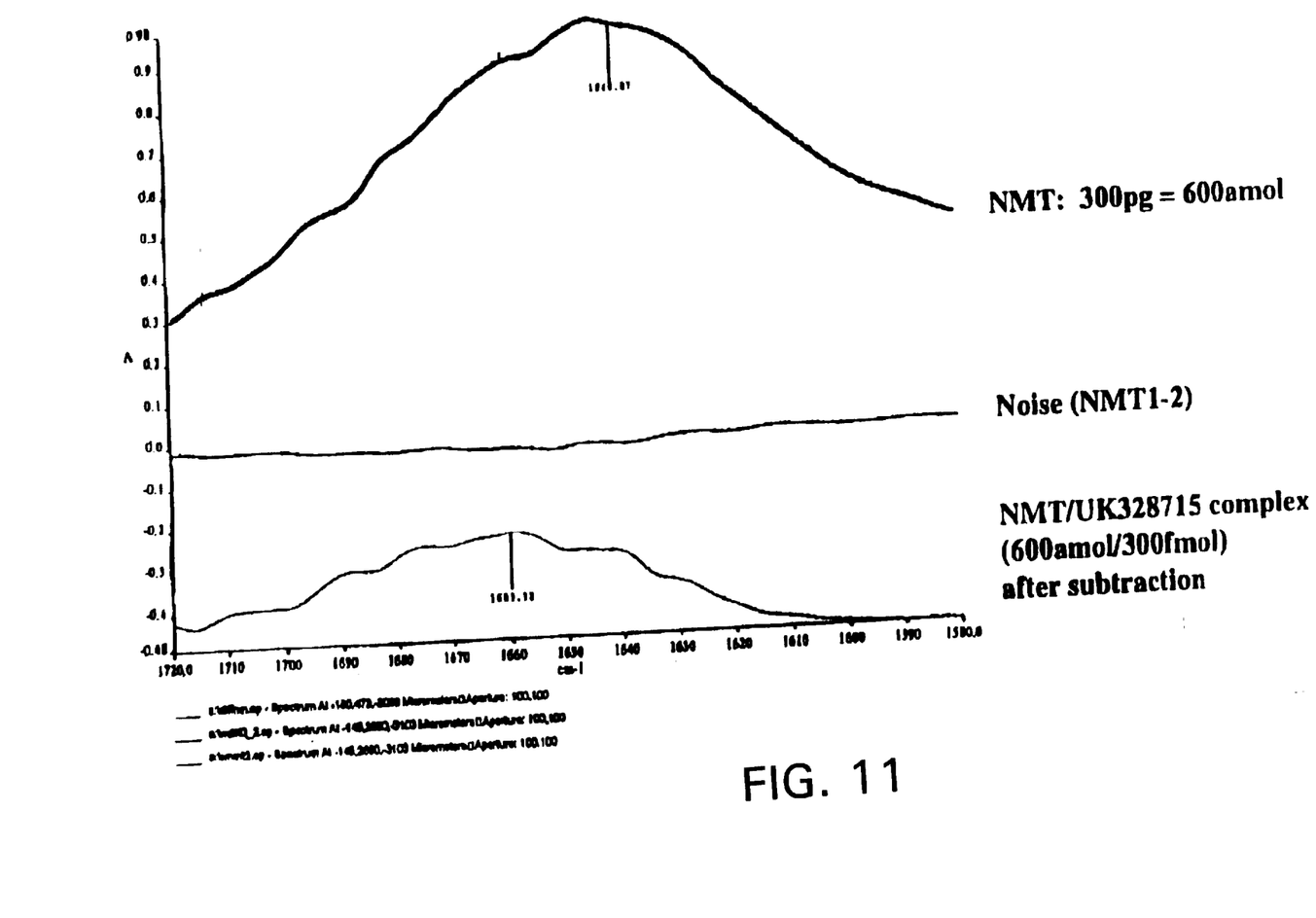
FIG. 11 shows the differential FT-IR (subtracted spectrum) of NMT/UK328715 minus the spectra of NMT and UK328715 individually.

Microscopic FT-IR was then used on a sample of UK328715 (100 pg, FIG. 8) and a mixture of NMT (300 pg) and UK328715 (100 pg), FIG. 9. The spectra of NMT (alone) and UK328715 (alone) was subtracted from the spectra of the mixture to obtain a difference spectra (FIGS. 10 and 11). The differential spectrum (>0) shows a peak shift from 1640.07 (NMT) to 1659.52 (NMT/UK328715) complex.

The results show that FT-IR spectroscopy, particularly microscopic FT-IR spectroscopy, can be used to identify the interactions of a compound with a biological macromolecule, even in complex mixtures and in fmolar amounts.

What we claim:

1. A method for determining whether a biological macromolecule binds to a compound, said method comprising the steps of:
   a) obtaining an FT-IR spectrum of a solution comprising said biological macromolecule and separately obtaining an FT-IR spectrum of a solution comprising said compound;
   b) obtaining an FT-IR spectrum of a solution comprising a mixture of said biological macromolecule and said compound;
   c) subtracting the FT-IR spectrum of the biological macromolecule and the FT-IR spectrum of the compound from the FT-IR spectrum of the mixture to determine a subtracted index;
   d) identifying a compound that binds to said biological macromolecule when the subtracted index of step c) is not equal to about 0,
   wherein said FT-IR spectrum is from about 1700 to about 1500 $cm^{-1}$ and the spectrum from about 2000 $cm^{-1}$ to about 1700 $cm^{-1}$ and the spectrum from about 1500 $cm^{-1}$ to about 1200 $cm^{-1}$ are used as a baseline noise reference.

2. The method of claim 1, wherein said compound is identified as binding to said biological macromolecule when the subtracted index of step c) yields a peak in the spectrum from about 1700 to about 1500 $cm^{-1}$ which is more than about two times greater than the baseline reference noise.

3. The method of claim 1, wherein said compound is identified as binding to said biological macromolecule when the subtracted index of step c) yields a peak in the spectrum from about 1700 to about 1500 $cm^{-1}$ which is more than about three times greater than the baseline reference noise.

4. The method of claim 1, wherein said biological macromolecule is a protein.

5. The method of claim 1, wherein said biological macromolecule is a substantially purified protein.

6. The method of claim 1, wherein said biological macromolecule is present in a complex mixture of about more than 10 biological macromolecules.

7. The method of claim 6, wherein said complex mixture of biological macromolecules is selected from the group consisting of, a cellular extract, a tissue extract, a fermentation broth of a microorganism, a fermentation broth of a cell culture and a fermentation broth of a tissue culture.

8. The method of claim 6, wherein said method is used to determine the presence or absence of a biological macromolecule in said complex mixture that binds to said compound.

9. The method of claim 1, wherein said compound is a substantially purified compound.

10. The method of claim 1, wherein said compound is present in a complex mixture of about more than 10 chemical entities.

11. The method of claim 5, wherein said complex mixture is selected from the group consisting of, a cellular extract, a tissue extract, a fermentation broth of a micro organism, a fermentation broth of a cell culture and a fermentation broth of a tissue culture.

12. The method of claim 11, wherein said complex mixture is a fermentation broth from a fungal culture.

13. The method of claim 10, wherein said method is used to determine the presence or absence of a compound in said complex mixture that binds to said biological macromolecule.

14. The method of claim 1, wherein said subtraction is done electronically using a computer controlled system.

15. The method of claim 1, wherein the binding of said compound to said biological macromolecule results in a spectral shift of from about >1 $cm^{-1}$ to about >5 $cm^{-1}$.

16. The method of claim 1, wherein said method uses microscopic FT-IR analysis.

17. The method of claim 16, wherein said method uses fmolar amounts of said biological macromolecule.

18. The method of claim 16, wherein said method uses fmolar amounts of said compound.

19. The method of claim 1, where said method is used to analyze more than 100 samples and FT-IR spectrum of each sample is obtained in about 1 second or less.

20. The method of claim 1, wherein said biological macromolecule is a drug target and said method is used to identify a potential therapeutic agent.

* * * * *